US011559286B2

United States Patent
Kamiyama et al.

(10) Patent No.: US 11,559,286 B2
(45) Date of Patent: Jan. 24, 2023

(54) ULTRASOUND DIAGNOSTIC APPARATUS AND CONTROL PROGRAM THEREOF FOR DETECTING THE THREE DIMENSIONAL SIZE OF A LOW ECHO REGION

(71) Applicant: General Electric Company, Schenectady, NY (US)

(72) Inventors: Naohisa Kamiyama, Tokyo (JP); Sayuka Saga, Tokyo (JP)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 17/023,478

(22) Filed: Sep. 17, 2020

(65) Prior Publication Data

US 2021/0093302 A1   Apr. 1, 2021

(30) Foreign Application Priority Data

Sep. 26, 2019   (JP) .............................. JP2019-174861

(51) Int. Cl.
*A61B 8/08* (2006.01)
*A61B 8/00* (2006.01)

(52) U.S. Cl.
CPC .......... *A61B 8/5223* (2013.01); *A61B 8/0825* (2013.01); *A61B 8/466* (2013.01); *A61B 8/5246* (2013.01); *A61B 8/485* (2013.01)

(58) Field of Classification Search
CPC ....... A61B 8/466; A61B 8/5246; A61B 8/485; A61B 8/0825; A61B 8/4245–4254; A61B 8/463; A61B 5/065
See application file for complete search history.

(56) References Cited

U.S. PATENT DOCUMENTS 6,102,861 A * 8/2000 Avila ..................... A61B 8/483
                                                     600/443
2003/0097068 A1 * 5/2003 Hossack .............. A61B 8/5276
                                                     600/443
(Continued)

FOREIGN PATENT DOCUMENTS

EP      1876567 A1 *  1/2008 ............... G06T 7/12
JP    2008079835 A     4/2008
(Continued)

OTHER PUBLICATIONS

JP-2018000339-A (Year: 2018).*
Japanese Application No. 2019-174861 filed Sep. 26, 2019—Notice of Preliminary Rejection dated Nov. 17, 2020; 2 pages.

*Primary Examiner* — Joel Lamprecht
*Assistant Examiner* — Nyrobi Celestine

(57) ABSTRACT

An ultrasound diagnostic apparatus and a control program for an ultrasound diagnostic apparatus. According to an embodiment, the ultrasound diagnostic apparatus includes an ultrasound probe that transmits and receives ultrasound waves to and from a subject in three dimensional space, a position sensor, and a processor. The processor is configured to determine whether or not a first region and a second region configure the same three dimensional region across a first scanning surface and a second scanning surface. The processor is configured to perform, based on the determining result, processing to obtain information representing the size of the three dimensional region in a direction intersecting the first scanning surface and the second scanning surface. The processor is configured to perform control for notifying the information.

17 Claims, 7 Drawing Sheets

(56) References Cited

U.S. PATENT DOCUMENTS

| | | | | |
|---|---|---|---|---|
| 2010/0331694 A1* | 12/2010 | Waki | ............ | A61B 8/08 |
| | | | | 600/443 |
| 2012/0265074 A1* | 10/2012 | Na | ............ | G06T 15/08 |
| | | | | 600/443 |
| 2013/0194267 A1* | 8/2013 | Tsujita | ............ | A61B 8/485 |
| | | | | 345/424 |
| 2013/0310690 A1* | 11/2013 | Chang | ............ | A61B 8/13 |
| | | | | 600/443 |
| 2015/0065877 A1* | 3/2015 | Orderud | ............ | A61B 8/466 |
| | | | | 600/438 |
| 2015/0366535 A1 | 12/2015 | Eggers | | |
| 2015/0374344 A1* | 12/2015 | Koide | ............ | G01S 7/52074 |
| | | | | 600/440 |
| 2016/0317130 A1* | 11/2016 | Auvray | ............ | A61B 8/461 |
| 2017/0281131 A1* | 10/2017 | Sendai | ............ | G16H 50/30 |
| 2019/0029651 A1* | 1/2019 | Patil | ............ | A61B 8/485 |
| 2020/0015786 A1* | 1/2020 | Duric | ............ | A61B 8/14 |

FOREIGN PATENT DOCUMENTS

| | | |
|---|---|---|
| JP | 2018000339 A | 1/2018 |
| JP | 2018-191779 A | 12/2018 |

\* cited by examiner

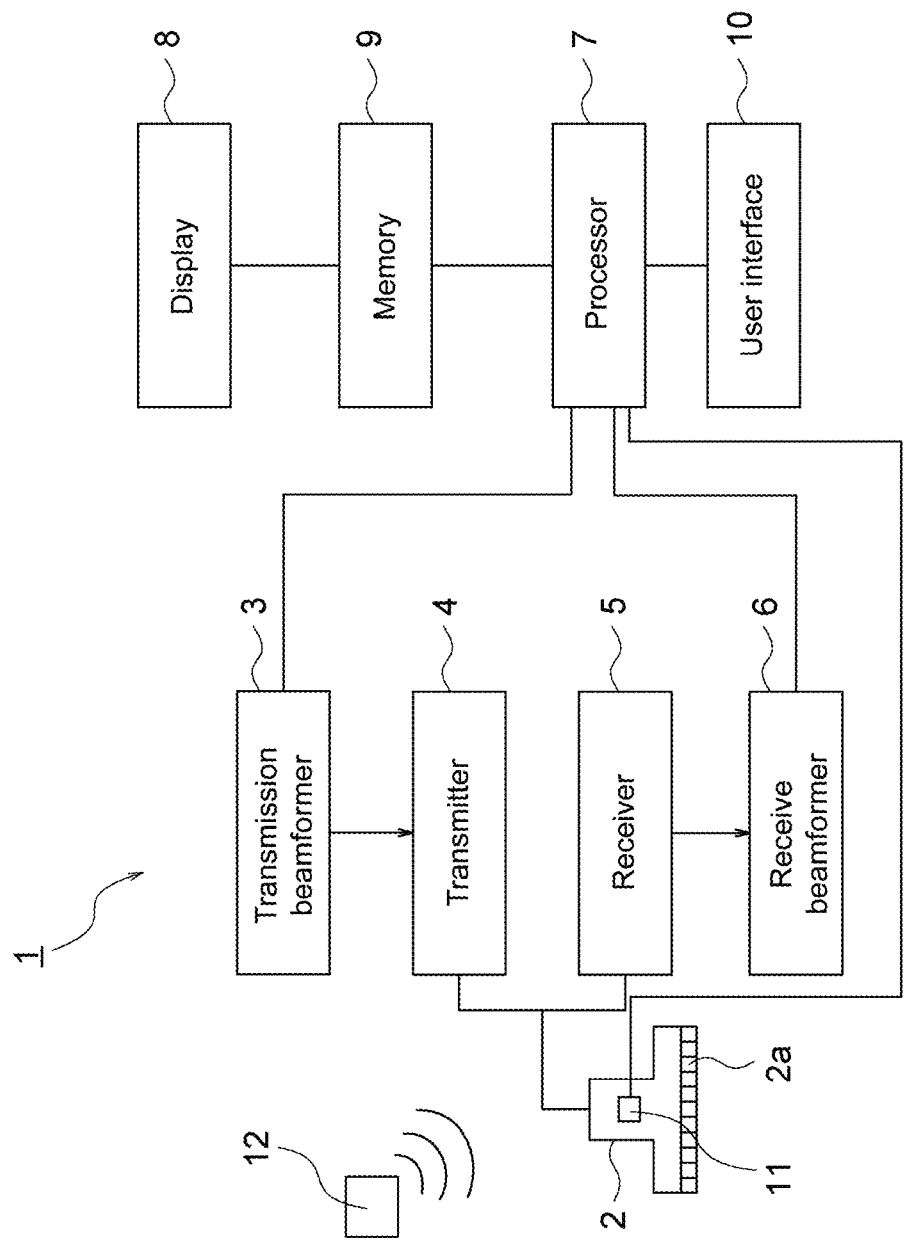
[Fig. 1]

[Fig. 2]
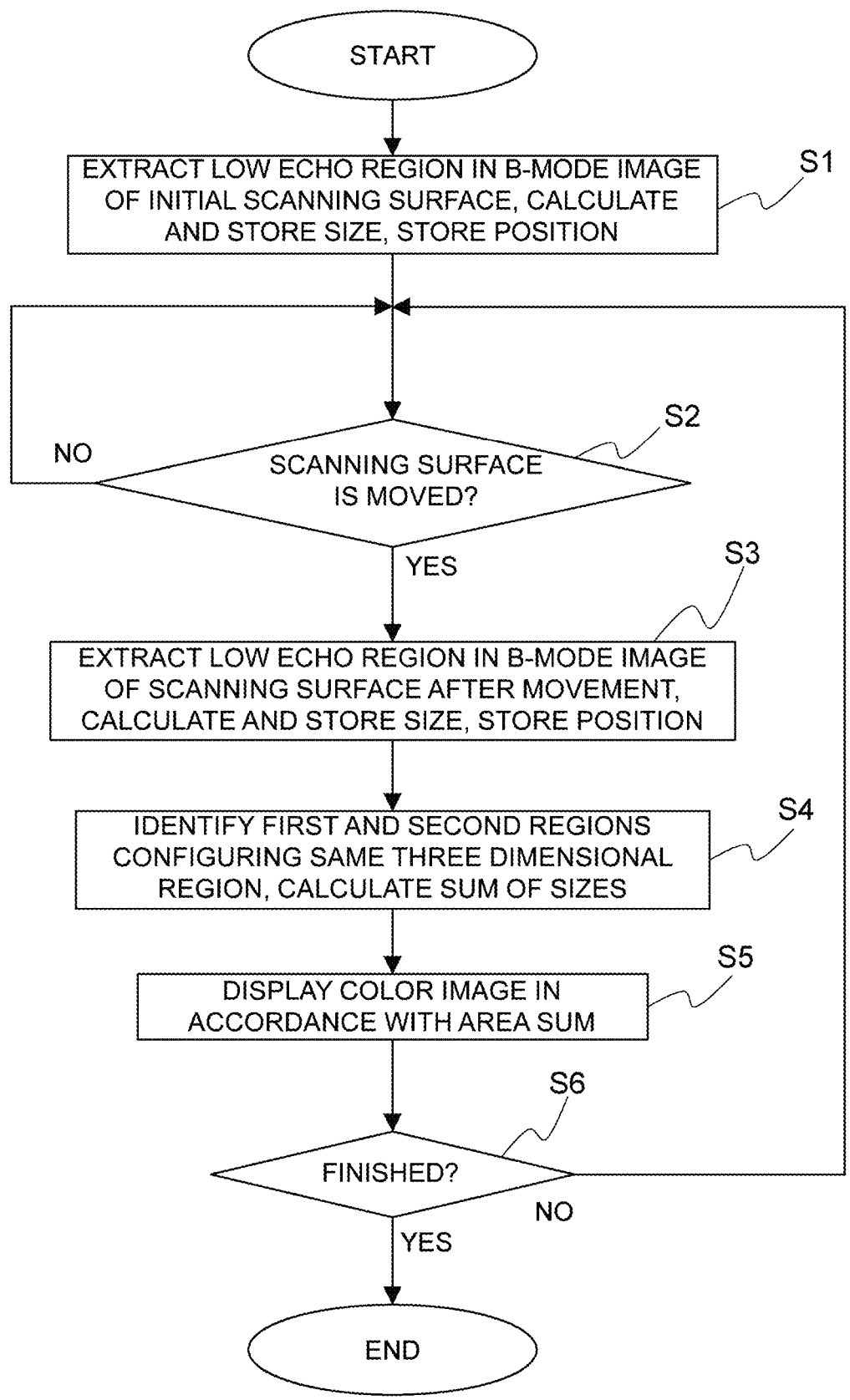

[FIG. 3]
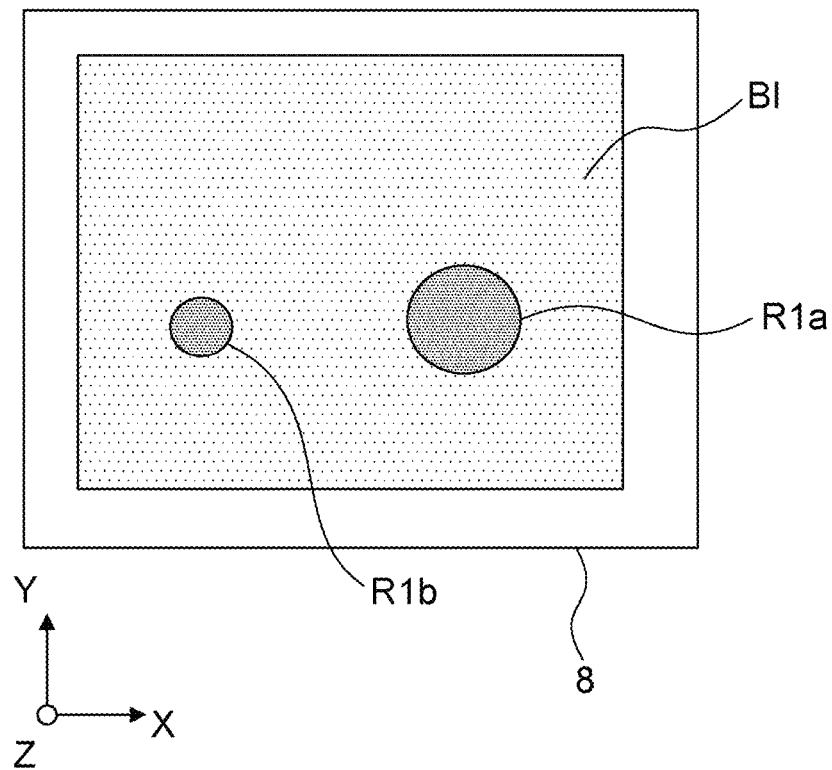
[FIG. 4]
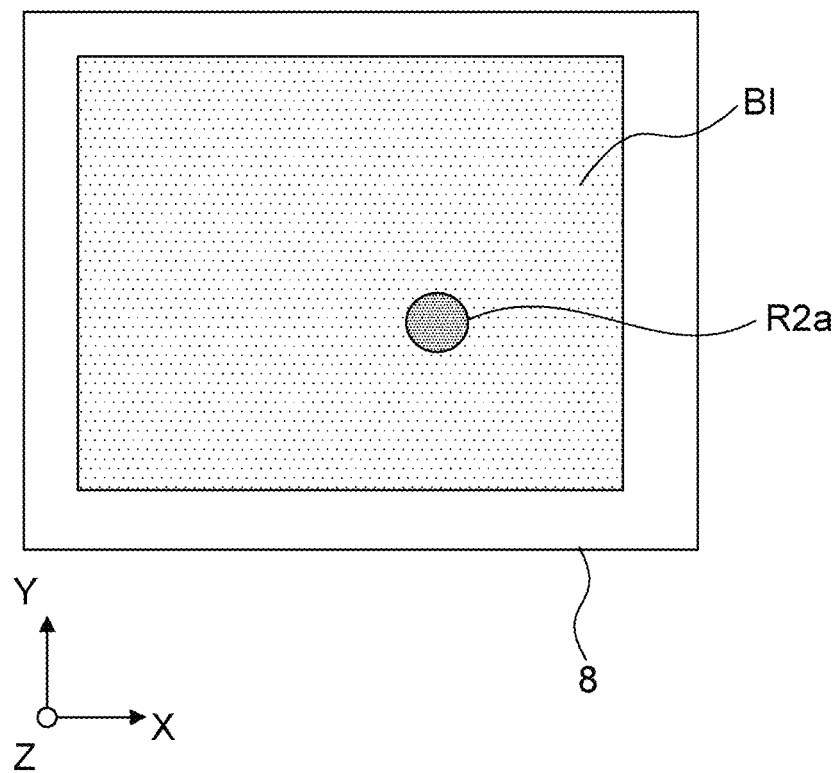

[FIG. 5]
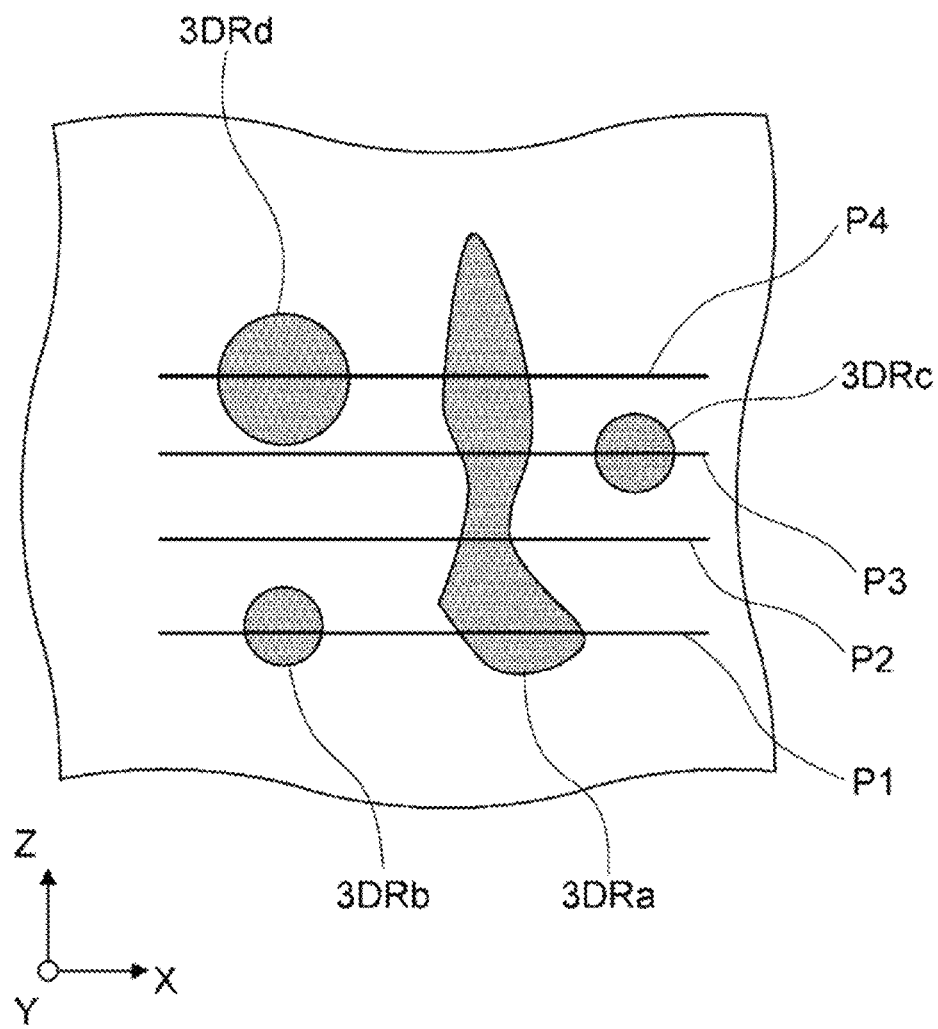

[FIG. 6]
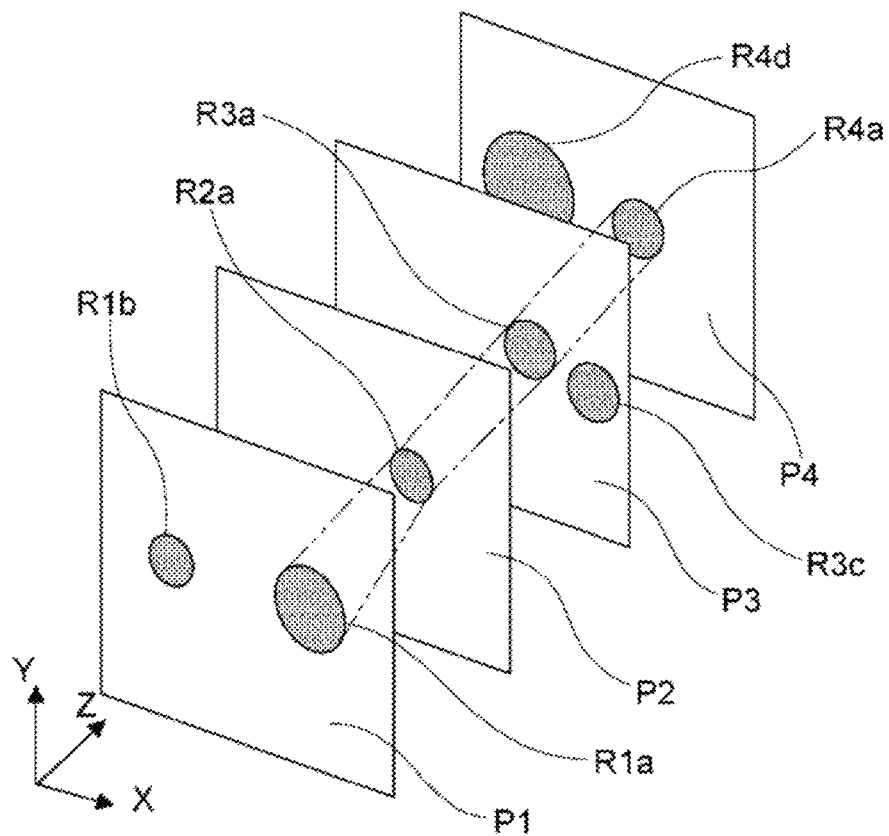
[FIG. 7]
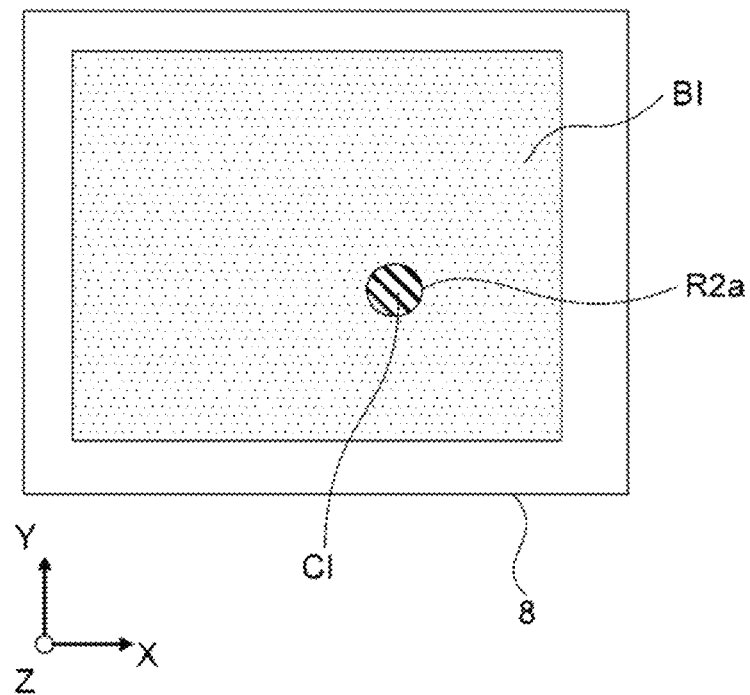

[Fig. 8]
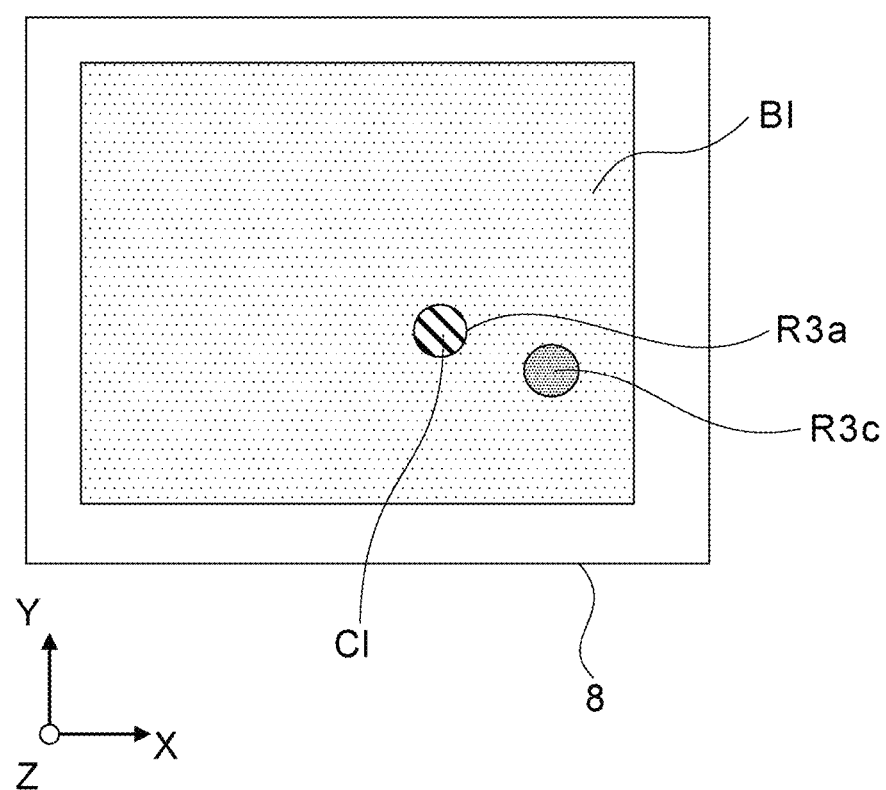

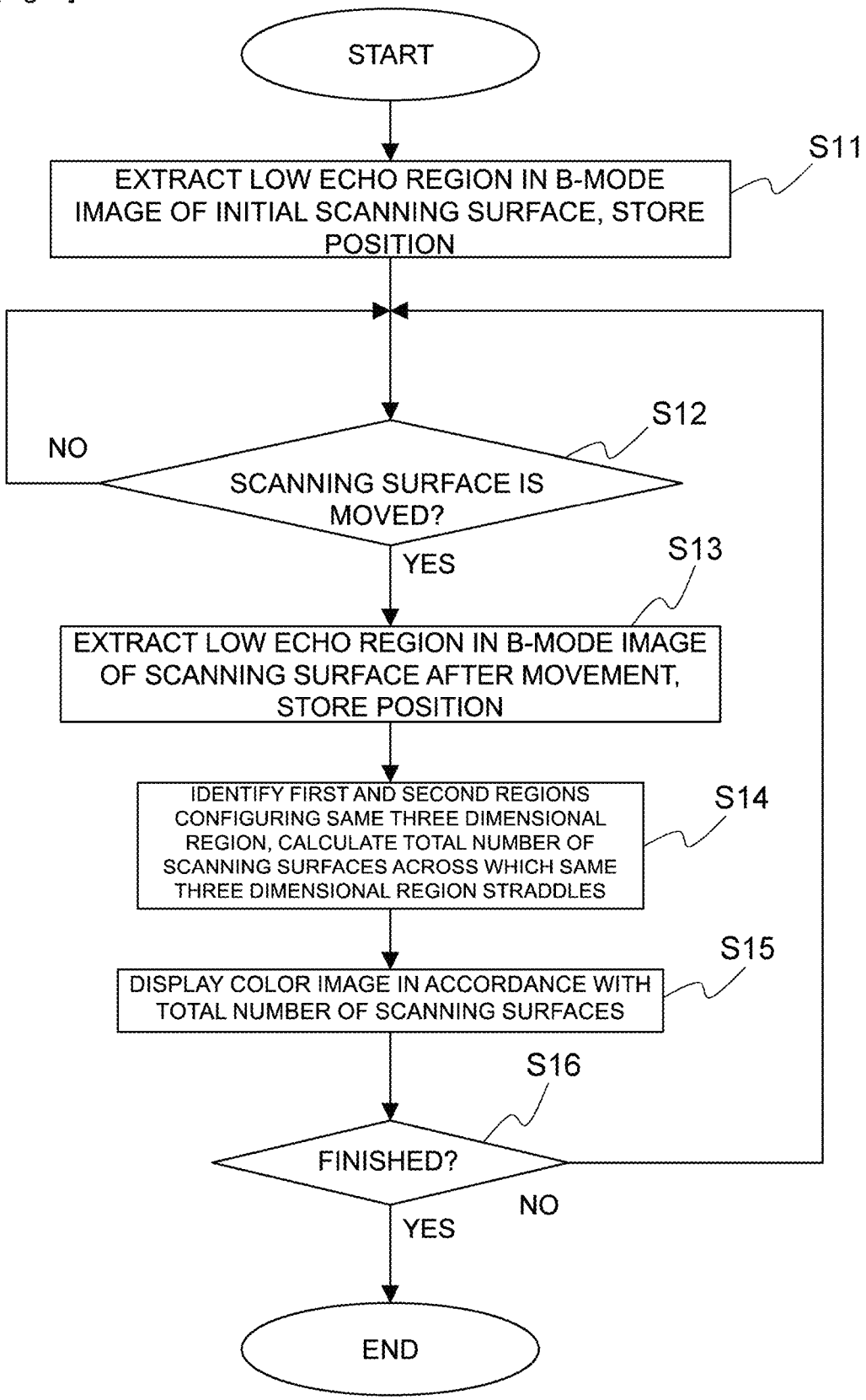

ULTRASOUND DIAGNOSTIC APPARATUS AND CONTROL PROGRAM THEREOF FOR DETECTING THE THREE DIMENSIONAL SIZE OF A LOW ECHO REGION

TECHNICAL FIELD

The present invention relates to an ultrasound diagnostic apparatus and a control program for creating ultrasound images of a subject.

BACKGROUND ART

Ultrasound diagnostic apparatuses are used in a variety of applications, taking advantage of the ability thereof to observe the cross-section of a subject in real time. For example, in recent years, ultrasound diagnostic apparatuses have become widely used as a means for breast cancer examinations other than mammography. Accordingly, there is a need to perform more accurate and speedy investigations. For example, with breast cancer examinations, elastography may be used in which ultrasound waves are implemented to measure the strain amount or elastic modulus of living tissues at an examination site and in which elastic images are displayed (for example, see Patent Document 1).

CITATION LIST

Patent Document

Patent Document 1 JP 2018-191779

SUMMARY OF THE INVENTION

Technical Problem

For breast cancer examinations, in addition to the elastography described above, diagnoses using B-mode images are also performed. In B-mode images of the breast, there are regions that differ in properties from the surrounding mammary gland tissue, referred to as low echo regions, that are less bright than their surroundings. Lesions in which these low echo regions appear include breast adenocarcinoma, non-invasive milk tube cancers, and invasive cancers with high intra-milk components, etc. In ultrasound examinations, a determination of being benign or of having malignant properties and the classification of a lesion are performed from the three dimensional form of the low echo region. If suspected of breast cancer, malignant masses, etc., the continuity of the low echo region is investigated in order to understand the degree of spread of the lesion. At this time, an evaluation of the continuity in the three dimensional direction orthogonal to the scanning surface of the ultrasound waves is not performed simply by observing two dimensional cross-sectional images, and therefore, there is a problem in that a lot of time and effort are required. Because the treatment method differs depending on the type and degree of progression of breast cancer, it is necessary to more easily and accurately understand the presence or absence and degree of continuity in the three dimensional direction of the low echo region.

Solution to Problem

One aspect of the invention made to solve the above problems includes an ultrasound diagnostic apparatus, including: an ultrasound probe that transmits and receives ultrasound waves to and from a subject in three dimensional space; a position sensor that detects the position of the ultrasound probe in three dimensional space; and a processor in which echo signals of the ultrasound waves received by the ultrasound probe and signals from the position sensor are input. Herein, the processor is configured to: create a first ultrasound image based on the echo signal obtained by transmitting and receiving the ultrasound waves at a first scanning surface by the ultrasound probe; extract a first region wherein the signal strength of the echo signals in the first ultrasound image is less than or equal to a threshold; create a second ultrasound image based on the echo signals obtained by transmitting and receiving the ultrasound waves at a second scanning surface by the ultrasound probe; determine, based on the signals from the position sensor, whether or not the first scanning surface and the second scanning surface are separated by a required distance; extract, when the first scanning surface and the second scanning surface are separated by a required distance, a second region wherein the signal strength of the echo signals in the second ultrasound image is less than or equal to a threshold; determine whether or not the first region and the second region configure the same three dimensional region across the first scanning surface and the second scanning surface; perform, based on the determination result, processing to obtain information representing the size of the three dimensional region in the direction intersecting the first scanning surface and the second scanning surface; and perform control for notifying the information.

Advantageous Effect of Invention

According to the present invention described above, the processor is configured to perform control for notifying information representing the size of the three dimensional region in the direction intersecting the first scanning surface and the second scanning surface, and it is thereby possible to easily and accurately understand the continuity of the low echo region in the direction intersecting the scanning surface.

BRIEF DESCRIPTION OF DRAWINGS

FIG. 1 is a block diagram illustrating a configuration of an example of the embodiment of an ultrasound diagnostic apparatus in the present invention.

FIG. 2 is a flow chart illustrating the process for displaying color images in the ultrasound diagnostic apparatus of the embodiment.

FIG. 3 is a diagram illustrating an example of a display in which a B-mode image having a low echo region is displayed.

FIG. 4 is a diagram illustrating another example of a display in which a B-mode image having a low echo region has been displayed.

FIG. 5 is an illustration of a three dimensional region.

FIG. 6 is an illustration of a three dimensional region.

FIG. 7 is a diagram illustrating an example of a display in which a color image is displayed.

FIG. 8 is a diagram illustrating an example of a display in which an updated color image has been displayed.

FIG. 9 is a flow chart illustrating the process for displaying color images in an ultrasound diagnostic apparatus of a variation of the embodiment.

DESCRIPTION OF EMBODIMENTS

A description will be given of an embodiment of the present invention. The ultrasound diagnostic apparatus 1 illustrated in FIG. 1 includes an ultrasound probe 2, a transmission beamformer 3, a transmitter 4, a receiver 5, a receive beamformer 6, a processor 7, a display 8, a memory 9, and a user interface 10.

The ultrasound probe 2 transmits and receives ultrasound waves to and from a subject in three dimensional space. As described in more detail, the transmission beamformer 3 and the transmitter 4 are configured to drive a plurality of vibrating elements 2a arranged in the ultrasound probe 2 to emit pulsed ultrasound signals to the subject (not shown). The pulsed ultrasound signals generate an echo that reflects within the subject and returns to the vibrating elements 2a. The echo is converted to electrical signals by the vibrating elements 2a which are received by the receiver 5. The electrical signals, that is, echo signals, representative of the received echo are input to the receive beamformer 6, after which receive beamforming is performed in this receive beamformer 6. The receive beamformer 6 may be adapted to output echo signals after receive beamforming to the processor 7.

The receive beamformer 6 may be a hardware beamformer or a software beamformer. If the receive beamformer 6 is a software beamformer, the receive beamformer 6 may include one or more processors, including any one or more of a graphics processing unit (GPU), a microprocessor, a central processing unit (CPU), a digital signal processor (DSP), or other types of processors capable of performing logical operations. A processor configuring the receive beamformer 6 may be configured by a processor different from the processor 7 or may be configured by the processor 7.

The ultrasound probe 2 may include electrical circuitry for performing all or a portion of transmission beamforming and/or receive beamforming. For example, all or a portion of the transmission beamformer 3, the transmitter 4, the receiver 5, and the receive beamformer 6 may be provided in the ultrasound probe 2.

The ultrasound probe 2 is provided with a magnetic sensor 11 configured by, for example, a Hall element. The magnetic sensor 11 detects magnetism generated by a magnetic generating unit 12, for example, installed in three dimensional space, to detect the position of the ultrasound probe 2 in three dimensional space. The magnetic generating unit 12 is configured by, for example, a magnetic generating coil. Detection signals at the magnetic sensor 11 are input to the processor 7. Detection signals at the magnetic sensor 11 may be input to the processor 7 via a cable (not shown) or may be wirelessly input to the processor 7. The processor 7 detects the position of the ultrasound probe 2 based on the detection signals of the magnetic sensor 11 and calculates the position of the scanning surface of the ultrasound waves in three dimensional space. The magnetic sensor 11 is an exemplary embodiment of a position sensor in the present invention. However, in the present invention, the position sensor for detecting the position of the ultrasound probe 2 is not limited to a magnetic sensor.

The processor 7 controls the transmission beamformer 3, the transmitter 4, the receiver 5, and the receive beamformer 6. The processor 7 is in electronic communication with the ultrasound probe 2. The processor 7 may control the ultrasound probe 2 to acquire the echo signals. The processor 7 controls which element of the vibrating elements 2a is active and the shape of the ultrasound beam transmitted from the ultrasound probe 2. The processor 7 is also in electronic communication with the display 8 and may be an ultrasound image for processing the echo signals to be displayed on the display 8. The term "electronic communication" may be defined to include both wired and wireless communications. The processor 7 may include a central processing unit (CPU) according to one embodiment. According to other embodiments, the processor 7 may include other electronic components that may perform processing functions such as a digital signal processor, a field programmable gate array (FPGA), a graphics processing unit (GPU), or other types of processors. According to other embodiments, the processor 7 may include a plurality of electronic components capable of performing processing functions. For example, the processor 7 may include two or more electronic components selected from a list of electronic components including a central processing unit, a digital signal processor, a field programmable gate array, and a graphics processing unit.

The processor 7 may also include a complex demodulator (not shown) that demodulates RF data. In another embodiment, demodulation may be performed early in the processing chain.

The processor 7 is configured to perform one or more processing operations in the data in accordance with the plurality of selectable ultrasound modalities. When echo signals are received, the data may be processed in real time during a scan session. For the purpose of this disclosure, the term "real time" is defined to include procedures that are performed without any deliberate delay.

The data may also be temporarily stored in a buffer (not shown) during scanning of the ultrasound waves and may be processed in live or off line operations rather than real time. In this disclosure, the term "data" may be used to refer to one or more data sets acquired using an ultrasound apparatus.

Raw data obtained by processing with the receive beamformer 6 may be processed by the processor 7 in other or different mode-related modules (e.g., B-mode, color Doppler, M-mode, color M-mode, spectral Doppler, elastography, TVI, strain, strain rate, etc.) to produce data for the ultrasound images. For example, one or more modules may generate ultrasound images such as B-mode, color Doppler, M-mode, color M-mode, spectral Doppler, elastography, TVI, strain, strain rate, and combinations thereof. An image beam and/or an image frame may be saved and timing information may be recorded indicating when the data is retrieved to the memory. The module may include, for example, a scan conversion module that performs a scan conversion operation to convert an image frame from a coordinate beam space to display space coordinates. A video processor module may be provided that reads the image frame from the memory while the procedure is being performed on the subject, displaying the image frame in real time. The video processor module may save the image frame in an image memory, wherein ultrasound images are read from the image memory and displayed on the display 8.

If the processor 7 includes a plurality of processors, the abovementioned processing tasks assigned by the processor 7 may be responsible for the plurality of processors. For example, the first processor may be used to demodulate and decimate RF signals, while the second processor may be used to further process the data and then display images.

Moreover, for example, if the receive beamformer 6 is a software beamformer, its processing function may be performed via a single processor or via a plurality of processors.

The display 8 is an LED (Light Emitting Diode) display, an LCD (Liquid Crystal Display), an organic EL (Electro-Luminescence) display, etc.

The memory 9 is any known data storage medium, including a non-transitory storage medium and a transient storage medium. The non-transitory storage medium is, for example, a non-volatile storage medium such as a Hard Disk Drive (HDD) drive, a Read Only Memory (ROM), etc. The non-transitory storage medium may include a portable storage medium such as a Compact Disk (CD) or a Digital Versatile Disk (DVD). Programs executed by the processor 7 are stored in the non-transitory storage medium.

The transitory storage medium is a volatile storage medium such as a Random Access Memory (RAM).

The user interface 10 may accept the input of the operator. For example, the user interface 10 accepts instructions and information input from a user. The user interface 10 is configured to include a keyboard, hard keys, a trackball, a rotary control, soft keys, etc. The user interface 10 may include a touch screen that displays soft keys, etc.

Next, the actions of the present example will be described. In the present example, the color image CI illustrated in FIG. 7 to be described later is displayed in order to more easily and accurately understand the three dimensional continuity of the low echo region. For example, when the user interface 10 accepts an input that transitions to a mode displaying the color image CI, processing of the flowchart illustrated in FIG. 2 is initiated. After an input is entered by the user to transmit and receive ultrasound waves to and from the subject by the ultrasound probe 2 to display the B-mode image on the display 8, the user may enter an input that transitions to the abovementioned mode.

In FIG. 2, first, in step S1, the processor 7 extracts a low echo region in which the signal strength of the echo signals in the B-mode image BI is less than or equal to a threshold. The processor 7 extracts the low echo region based on either the raw data or the image data. As illustrated in FIG. 3, for example, the processor 7 extracts regions R1a, R1b, which are low echo regions in which the luminance is lower than the surroundings in the B-mode image BI. The B-mode image BI in step S1 is an example of a first ultrasound image in the present invention. Furthermore, the scanning surface in which the transmission and reception of ultrasound waves is performed to create the B-mode image BI in step S1 is an example of a first scanning surface in the present invention. Moreover, the regions R1a, R1b are examples of embodiments of first regions in the present invention.

In the present example, the scanning surface of the B-mode image BI in which the regions R1a, R1b have been extracted in step S1 is referred to as the initial scanning surface. Furthermore, the scanning surface before the low echo region is extracted and the movement determination is performed in step S2, described later, is referred to as the scanning surface before movement. This scanning surface before movement is referred to as the first scanning surface, with the low echo region extracted at the first scanning surface referred to as the first region. Also, the ultrasound image for the first scanning surface is referred to as the first ultrasound image.

Moreover, in step S1, the processor 7 calculates the sizes of the regions R1a, R1b. In this example, the number of pixels in the regions R1a, R1b in the B-mode image BI is calculated. The processor 7 then stores, in the memory 9, the positions and sizes (the number of pixels) of the regions R1a, R1b in the B-mode image BI. The processor 7 performs labeling to apply identification information on both the regions R1a, R1b and stores the regions in the memory 9.

Further, in step S1, the processor 7 stores, in the memory 9, the position of the scanning surface where the B-mode image BI in which the regions R1a, R1b have been extracted was obtained. The processor 7 calculates the position of the scanning surface in three dimensional space where the B-mode image BI in which the regions R1a, R1b have been extracted was obtained based on the detection signals of the magnetic sensor 11, and stores the position in the memory 9.

Next, in step S2, the processor 7 determines the presence or absence of movement of the scanning surface. The processor 7 determines whether or not the real time scanning surface has moved from the scanning surface of the B-mode image BI in which the low echo region has been extracted. The real time scanning surface is the scanning surface in which the B-mode image BI of the latest frame has been obtained. For example, the processor 7 determines the presence or absence of the movement of the scanning surface described above by determining whether or not the distance between the scanning surface in which the latest frame B-mode image BI has been obtained and the scanning surface (first scanning surface) of the B-mode image BI in which the regions R1a, R1b have been extracted are separated by a required distance. The position of the scanning surface in which the B-mode image BI of the latest frame has been obtained is the position obtained based on the detection signals of the magnetic sensor 11. The position of the scanning surface of the B-mode image BI in which the regions R1a, R1b have been extracted is the position of the scanning surface stored in the memory 9.

The processor 7 may calculate, for example, the distance between at least one point on the scanning surface in which the B-mode image BI of the current frame has been obtained and at least one point on the scanning surface of the B-mode image BI in which the regions R1a, R1b have been extracted as the distance between the two scanning surfaces and then determine whether or not the abovementioned required distance is had. The points of interest for the distance calculation are the points corresponding to the two scanning surfaces, that is, the points configuring the same pixels. The processor 7 may calculate the distance for each of the corresponding plurality of points, rather than one corresponding point in the two scanning surfaces, and then calculate the distance of the two scanning surfaces using these distances.

The required distance used in step S2 is stored in the memory 9.

In step S2, in the event it is determined that the scanning surface has moved ("YES" in step S2), the processing transitions to step S3. On the other hand, in the event it is determined in step S2 that the scanning surface has not moved ("No" in step S2), the processing in step S2 is repeated.

Next, in step S3, the processor 7 extracts the low echo region in which the signal strength of the echo signals in the B-mode image BI is less than or equal to the threshold, via a similar manner to step S1. As illustrated in FIG. 4, for example, the processor 7 extracts a region R2a, which is the low echo region in which the luminance is lower than the surrounding area in the B-mode image BI. The scanning surface of the B-mode image BI in which the region R2a has been extracted in step S3 is the real time scanning surface determined to have been moved in step S2, which is an example of the second scanning surface in the present invention. In addition, the region R2a is an example of an embodiment of the second region in the present invention. In the present example, in step S2, the scanning surface that is the object of determination of the presence or absence of movement with respect to the first scanning surface is referred to as the second scanning surface, while the low echo region extracted at the second scanning surface, which is determined to have been moved, is referred to as a second region.

The B-mode image BI in step S3 is a real time scanning surface determined to have been moved, that is, a B-mode image for the second scanning surface in step S2, and is an example of a second ultrasound image in the present invention.

Moreover, in step S3, the processor 7 calculates the size of the region R2a. In this example, the number of pixels in the region R2a in the B-mode image BI is calculated. The processor 7 then stores, in the memory 9, the position and size (the number of pixels) of the region R2a in the B-mode image BI.

Further, in step S3, the processor 7 stores, in the memory 9, the position where the B-mode image BI in which the region R2a has been extracted was obtained. For example, the processor 7 stores, in the memory 9, the position of the scanning surface in three dimensional space where the B-mode image BI in which the region R2a has been extracted was obtained. The position of the scanning surface in three dimensional space where the B-mode image BI in which the region R2a has been extracted was obtained is a position obtained based on the detection signals of the magnetic sensor 11.

Next, in step S4, the processor 7 identifies the first region and the second region that configure the same three dimensional region across the first scanning surface and the second scanning surface. The processor 7 determines whether or not the regions R1a, R1b and the region R2a configure the same three dimensional region across the first scanning surface and the second scanning surface, then performs the above-mentioned identification.

The three dimensional region is a three dimensional region of the low echo region. Specifically, the three dimensional region will be described based on FIGS. 5 and 6. In FIGS. 5 and 6, the X direction corresponds to the azimuth direction (the arrangement direction of the vibrating elements 2a), while the Z direction is the elevation direction. Furthermore, the Y direction is the direction orthogonal to the X direction and the Z direction and is the depth direction in the subject. For convenience of explanation, X, Y, and Z directions are also illustrated in FIGS. 3 and 4.

FIG. 5 shows three dimensional regions 3DRa, 3DRb, 3DRc, and 3DRd on the XZ plane in the subject. Note that FIG. 6 illustrates cross sections (portions corresponding to the regions R1a, R1b, R2a, R3a, R3c, R4a, and R4d to be extracted in the B-mode image BI) of the three dimensional regions 3DRa, 3DRb, 3DRc, and 3DRd on scanning surfaces P1 to P4 described below.

Reference signs P1 and P2 denote scanning surfaces that extend in the XY-plane direction. Here, the scanning surface P1 is the initial scanning surface in step S1 and is the first scanning surface. In addition, here, the scanning surface P2 is a scanning surface after movement and is the second scanning surface.

Note that reference signs P3 and P4 also denote scanning surfaces. The scanning surfaces P3 and P4 are described below.

The regions R1a, R1b are the low echo regions in the B-mode image BI for the scanning surface P1. The region R2a is the extracted low echo region in the B-mode image BI for the scanning surface P2. The region R1a and region R2a configure the three dimensional region 3DRa. In addition, the region R1b configures the three dimensional region 3DRb.

The three dimensional region 3DRa straddles the scanning surfaces P1 to P4 and is longer in the Z direction than the three dimensional region 3DRb. The three dimensional region 3DRa that is a relatively long low echo region in the direction intersecting the scanning surface in this manner is a region that is likely to be a lesion. On the other hand, the three dimensional regions 3DRb, 3DRc, and 3DRd are regions of normal tissue.

In the B-mode image for the first scanning surface and the B-mode image for the second scanning surface, the processor 7 determines that the first region and the second region having common pixels configure the same three dimensional region. The processor 7 reads the positions of the first region and second region from the memory 9 to identify the first region and the second region having common pixels. Here, the processor 7 reads the positions of the regions R1a, R1b and the position of the region R2a from the memory 9 to identify the region Ma and the region R2a as regions having common pixels. Further, it determines that these region Ma and region R2a configure the same three dimensional region 3DRa across the scanning surfaces P1, P2.

The processor 7 stores the same identification information as the region Ma in the memory 9 as identification information in the region R2a. The identification information of the regions R1a, R2a may be referred to as identification information of the three dimensional region 3DRa.

The processor 7 also adds the number of pixels in the regions R1a, R2a and stores the same in the memory 9 as the sum Spi of the sizes of the regions R1a, R2a. The sum Spi is stored in association with the identification information of the regions R1a, R2a. The sum Spi is an example of an embodiment of information representing the size of the three dimensional region in the present invention.

Next, in step S5, as illustrated in FIG. 7, the processor 7 causes the display 8 to display the color image CI in accordance with the sum Spi. The processor 7 causes the color image CI to be displayed in the region where the sum Spi has been obtained. Here, the processor 7 causes the color image CI to be displayed in the region R2a in the B-mode image BI.

The color image CI is configured by colors having different degrees of saturation depending on the sum Spi, etc. However, it is sufficient that the color image CI has a display form in accordance with the sum Spi and, for example, the color image CI may be configured by a color having different lightness depending on the sum Spi. The color image CI is an example of an embodiment of information representing the image in accordance with the size of the three dimensional region and the size of the three dimensional region in the present invention.

For example, the processor 7 creates and displays a color image CI using a color map stored in the memory 9. The color map defines the saturation and lightness in accordance with the sum Spi. The color map may be set such that color of the color image CI appears not to be displayed until the sum Spi is greater than the required value.

Next, in step S6, the processor 7 determines whether or not processing is finished. For example, in the event the user interface 10 receives an input that finishes the processing by the user, the processor 7 determines that processing is finished ("YES" in step S6).

On the other hand, in the event the processor 7 determines that processing is not finished ("NO" in step S6), the processing returns to step S2. In this step S2, the processor 7 performs the movement determination on the basis of the new frame. Specifically, the processor 7 sets the second scanning surface in which the extraction of the second region has been performed in the step S3 immediately prior as the first scanning surface and determines whether or not the distance between this first scanning surface and the second scanning surface in which the B-mode image BI of the new frame has been obtained has the required distance. Here, the processor 7 sets the scanning surface P2 as the first scanning surface and determines whether or not the distance between this scanning surface P2 and the second scanning surface in which the B-mode image BI of the new frame has been obtained has the required distance.

A scanning surface determined to have the required distance from the scanning surface P2 is set as the scanning surface P3 illustrated in FIGS. 5 and 6. In other words, the scanning surface P3 is the second scanning surface. In step S3, the processor 7 extracts the low echo region in the B-mode image BI of the scanning surface P3. Here, the regions R3a, R3c are extracted as low echo regions. The processor 7 stores, in the memory 9, the number of pixels in the regions R3a, R3c and the position in the B-mode image BI. The processor 7 also stores, in the memory 9, the position at which the B-mode image BI in which the regions R3a, R3c have been extracted was obtained.

In step S4, the processor 7 determines whether or not the region R2a and the regions R3a, R3c configure the same three dimensional region across the scanning surfaces P2, P3. Here, the region R2a is the first region and the regions R3a, R3c are the second regions. Further, the region R2a and the region R3a have common pixels. The processor 7 determines that the region R2a and the region R3a configure the same three dimensional region 3DRa. Note that the region R3c configures the three dimensional region 3DRc.

The processor 7 stores the same identification information as the regions Ma, R2a in the memory 9 as identification information in the region R3a. The processor 7 also stores the identification information in the region R3c in the memory 9.

Furthermore, the processor 7 adds the sum Spi of the number of pixels in the regions R1a, R2a stored in the memory 9 plus the number of pixels in the region R3a to obtain a new sum Spi and stores the same in the memory 9 in association with the identification information.

In step S5, the color image CI is updated to the color in accordance with the newly obtained sum Spi. As illustrated in FIG. 8, the updated color image CI is displayed in the region R3a in the B-mode image BI.

In step S6, once it has been determined again that processing is not finished and returns again to step S2, the processing after step S2 is performed again in the same manner as described above. Here, the first scanning surface is the scanning surface P3, while the second scanning surface is the scanning surface P4. The low echo regions in the B-mode image BI of the scanning surface P4 are the regions R4a, R4d. The region R4a configures the three dimensional region 3DRa, while the region R4d configures the three dimensional region 3DRd. The processor 7 determines that the region R3a and the region R4a configure the same three dimensional region 3DRa across the scanning surfaces P3, P4 and stores the same identification information as the regions R1a, R2a, and R3a in the memory 9 as identification information in the region R4a.

The processor 7 adds the sum Spi of the number of pixels in the regions R1a, R2a, and R3a stored in the memory 9 plus the number of pixels in the region R4a to obtain a new sum Spi and stores the same in the memory 9, updating the color image CI. Although not specifically illustrated, the updated color image CI is displayed in the region R4a in the B-mode image BI.

According to the present example, a color image CI having a color in accordance with the sum of the number of pixels in the low echo regions configuring the three dimensional region 3DRa is displayed. Therefore, the color image CI is displayed in a color having saturation, etc. in accordance with the size of the three dimensional region 3Dra in the direction intersecting the scanning surfaces P1 to P4, making it possible to easily and accurately understand the continuity of the low echo region in the direction intersecting the scanning surface.

Although only four scanning surfaces P1 to P4 are illustrated in the present example, these are merely examples. The color image CI may be displayed by performing extraction of the low echo region in the scanning surfaces that are narrower than the intervals between each of the scanning surfaces P1 to P4 and have more scanning surfaces.

Next, a variation of the embodiment will be described. In this variation, when the user interface 10 accepts an input that transitions to a mode displaying the color image CI, processing of the flowchart illustrated in FIG. 9 is initiated.

In FIG. 9, first, in step S11, similar to step S1, the processor 7 extracts the regions R1a, R1b which are the low echo regions in which the signal strength of the low echo signal in the B-mode image BI for the scanning surface P1 is less than or equal to the threshold.

Even in step S11, similar to step S1, processor 7 stores, in the memory 9, the positions and identification information of the regions R1a, R1b in the B-mode image BI. Also, similar to step S1, the processor 7 stores, in the memory 9, the position at which the B-mode image BI in which the regions R1a, R1b have been extracted was obtained. However, in this variation, the calculation of the sizes of the regions R1a, R1b is not performed.

Next, in step S12, the processor 7 determines the presence or absence of movement of the scanning surface in the same manner as in step S2. Next, in step S13, similar to step S3, the processor 7 extracts the region R2a, which is a low echo region, in the B-mode image BI for the scanning surface P2. Similar to step S3, the processor 7 also stores, in the memory 9, the position of the region R2a in the B-mode image BI. Moreover, similar to step S1, the processor 7 stores, in the memory 9, the position at which the B-mode image BI in which the region R2a has been extracted was obtained.

Next, in step S14, similar to step S4, the processor 7 determines that the region R1a and the region R2a configure the same three dimensional region 3DRa across the scanning surfaces P1, P2. Storing the identification information for the region R2a is also performed in the same manner as in step S4.

The processor 7 calculates a total number Spl of scanning surfaces across the three dimensional region 3DRa based on the determination described above and stores it in the memory 9. Here, the total number Spl is "2". The total number Spl is also stored in association with the identification information of the regions R1a, R2a. The total number Spl is an example of an embodiment of information representing the size of the three dimensional region in the present invention.

Next, in step S15, similar to step S5, the color image CI is displayed on the display 8. However, in this variation, the color image CI is an image having a color in accordance with the total number Spl of the scanning surfaces across which the same three dimensional region straddles. Here, the color image CI having a color in accordance with the total number Spl of the scanning surfaces across the three dimensional region 3DRa is displayed in the region R2a in the B-mode image BI.

The color image CI has a saturation, lightness, etc. in accordance with the total number Spl across which the same three dimensional region straddles. In this variation, the color map defines the saturation and lightness in accordance with the total number Spl.

In step S16, completion determination processing similar to step S6 is performed. In the event it is determined that processing is not finished, the processing returns to step S12 and after the movement determination has been performed again in the same manner as in step S2, the regions R3a, R3c, which are the low echo regions in the scanning surface P3, are extracted in step 13.

In step S13, if the positions of the regions R3a, R3c in the B-mode image BI and the position in which the B-mode image BI has been obtained are stored in the memory 9, the processing transitions to the processing in step S14. In this step S14, similar to step S4, the processor 7 determines that the region R2a and the region R3a configure the same three dimensional region 3DRa across the scanning surfaces P2, P3. Further, the identification information of the regions R3a, R3c is stored in the same manner as in step S4.

Furthermore, the processor 7 adds "1" to the "2" that is the total number Spl of the scanning surfaces across the three dimensional region 3DRa stored in the memory 9 to obtain the "3" as a new total number Spl and stores the "3" in the memory 9.

In step S15, the processor 7 updates the color image CI to a color in accordance with the newly obtained total number Spl of the scanning surfaces. The updated color image CI is displayed in the region R3a.

In step S16, once it has again been determined that processing is not finished and returns again to step S12, the processing after step S12 is performed again in the same manner as described above. Here, in step S14, the processor 7 adds "1" to the "3" that is the total number Spl of the scanning surfaces stored in the memory 9 to obtain the "4" as a new total number Spl and stores the "4" in the memory 9. Further, the color image CI is updated to a color in accordance with the new total number of Spl. The updated color image CI is displayed in the region R4a.

According to this variation, the color image CI having a color in accordance with the total number Spl of the scanning surfaces across the three dimensional region 3DRa is displayed, making it possible to easily and accurately understand the continuity of the low echo region in the direction intersecting the scanning surface.

The present invention has been described above on the basis of the foregoing embodiment; however, it goes without saying that various modifications and variations may be made without departing from the scope of the present invention. For example, the flowcharts described in the embodiments described above are exemplary and flexible so long as the spirit in the present invention is not lost.

Further, the above embodiments may include:
a method for controlling an ultrasound diagnostic apparatus, the apparatus including: an ultrasound probe that transmits and receives ultrasound waves to and from a subject in three dimensional space;
a position sensor that detects the position of the ultrasound probe in three dimensional space; and a processor in which echo signals of the ultrasound waves received by the ultrasound probe and signals from the position sensor are input;
wherein the processor is configured to:
create a first ultrasound image based on the echo signals obtained by transmitting and receiving the ultrasound waves at a first scanning surface by the ultrasound probe;
extract a first region wherein the signal strength of the echo signals in the first ultrasound image is less than or equal to a threshold;
create a second ultrasound image based on the echo signals obtained by transmitting and receiving the ultrasound waves at a second scanning surface by the ultrasound probe;
determine, based on the signals from the position sensor, whether or not the first scanning surface and the second scanning surface are separated by a required distance;
extract, when the first scanning surface and the second scanning surface are separated by the required distance, a second region wherein the signal strength of the echo signals in the second ultrasound image is less than or equal to a threshold;
determine whether or not the first region and the second region constitute the same three dimensional region across the first scanning surface and the second scanning surface;
perform, based on the determination result, processing to obtain information representing the size of the three dimensional region in the direction intersecting the first scanning surface and the second scanning surface; and
perform control for notifying the information.

Further, in the embodiment described above, while the case in which the ultrasound probe is moved in only one direction has been described as an example, if the ultrasound probe moves in the opposite direction to the required direction, it may be determined whether or not the scanning surface has been previously detected in the low luminance region based on the position information detected by the magnetic sensor. If the scanning surface has been previously detected in the low luminance region, adding the number of pixels or the number of scanning surfaces is not performed.

REFERENCE SIGNS LIST

1 Ultrasound diagnostic apparatus
2 Ultrasound probe
7 Processor
8 Display
9 Memory
11 Magnetic sensor

The invention claimed is:

1. An ultrasound diagnostic apparatus, comprising:
an ultrasound probe that transmits and receives ultrasound waves to and from a subject in three dimensional space;
a display;
a position sensor that detects the position of the ultrasound probe in three dimensional space; and
a processor in which echo signals of the ultrasound waves received by the ultrasound probe and signals from the position sensor are input;
wherein the processor is configured to:
create a plurality of ultrasound images, wherein each of the plurality of ultrasound images is based on echo signals obtained by transmitting and receiving the ultrasound waves at one of a plurality of scanning surfaces by the ultrasound probe, wherein each of the plurality of scanning surfaces is separated from the other of the plurality of scanning surfaces by a required distance;
extract a plurality of low echo regions from the plurality of ultrasound images, wherein the signal strength of the echo signals in each of the plurality of low echo regions is less than or equal to a threshold; identify two or more of the plurality of low echo regions that configure the same three dimensional region across two or more of the plurality of scanning surfaces;

perform processing to obtain information representing a size of the three dimensional region in a direction intersecting the two or more of the plurality of scanning surfaces;

cause the display to display a color image in a region of a B-mode image, wherein the B-mode image corresponds to one of the plurality of scanning surfaces, wherein the color image represents the three dimensional region within the one of the plurality of scanning surfaces, and wherein a color of the color image represents the size of the three dimensional region in the direction intersecting the two or more of the plurality of scanning surfaces.

2. The ultrasound diagnostic apparatus of claim 1, wherein the processor is configured to determine the size of the three dimensional region in the direction intersecting the two or more of the plurality of scanning planes by summing a number of pixels corresponding to the three dimensional region in the plurality of scanning surfaces.

3. The ultrasound diagnostic apparatus of claim 2, wherein the processor is configured to determine the color using a color map.

4. The ultrasound diagnostic apparatus of claim 3, wherein the color map defines the saturation and lightness of the color in accordance with a sum determined by summing the number of pixels corresponding to the three dimensional region in the plurality of scanning surfaces.

5. The ultrasound diagnostic apparatus of claim 1, wherein the processor is configured to determine the size of the three dimensional region in the direction intersecting the two or more of the plurality of scanning planes in accordance with a total number of the plurality of scanning surfaces across which the three dimensional region straddles.

6. The ultrasound diagnostic apparatus of claim 5, wherein the processor is configured to determine the color using a color map.

7. The ultrasound diagnostic apparatus of claim 6, wherein the color map defines a saturation and lightness of the color in accordance with the total number of the plurality of scanning surfaces across which the three dimensional region straddles.

8. The ultrasound diagnostic apparatus of claim 1, wherein the processor is further configured to:

create an additional ultrasound image based on additional echo signals obtained by transmitting and receiving, with the ultrasound probe, additional ultrasound waves at an additional scanning surface that is different than the plurality of scanning surfaces, wherein the additional scanning surface is separated from each of the plurality of scanning surfaces by the required distance;

identify an additional low echo region in the additional ultrasound image, wherein the additional low echo region and the two or more of the plurality of low echo regions configure the same three dimensional region;

perform processing to obtain information representing an updated size of the three dimensional region across both the plurality of scanning surfaces and the additional scanning surface;

cause the display to display an updated color image in an updated region of an updated b-mode image, wherein the updated b-mode image corresponds to the additional scanning surface, wherein the color image represents the three dimensional region within the additional scanning surface, and wherein the color image is shown in a different color than the color to represent the updated size of the three dimensional region across the plurality of scanning surfaces and the additional scanning surface.

9. The ultrasound diagnostic apparatus of claim 8, wherein the different color has a different saturation than the color.

10. The ultrasound diagnostic apparatus of claim 8, wherein the different color has a different lightness than the color.

11. The ultrasound diagnostic apparatus of claim 8, wherein the additional ultrasound image is a real time ultrasound image.

12. The ultrasound diagnostic apparatus of claim 1, wherein the plurality of scanning surfaces are parallel to each other.

13. The ultrasound diagnostic apparatus of claim 1, wherein the plurality of scanning surfaces are in an XY-plane, and wherein the direction intersecting the plurality of scanning surfaces is a Z direction, which is perpendicular to the XY-plane.

14. An ultrasound diagnostic apparatus, comprising:

an ultrasound probe that transmits and receives ultrasound waves to and from a subject in three dimensional space;

a display;

a memory;

a position sensor that detects the position of the ultrasound probe in three dimensional space; and a processor, wherein the processor is configured to:

acquire echo signals from a plurality of scanning surfaces, wherein each of the plurality of scanning surfaces are separated from the other of the plurality of scanning surfaces by a required distance; store, in the memory, a position associated with each of the plurality of scanning surfaces based on signals from the position sensor;

create a plurality of ultrasound images based on the echo signals, wherein each of the plurality of ultrasound images represents a different one of the plurality of scanning surfaces;

extract a plurality of low echo regions in the plurality of ultrasound images, wherein each of the plurality of low echo regions is associated with a three dimensional region intersecting two or more of the plurality of scanning surfaces;

calculate a size of each of the plurality of low echo regions in the plurality of ultrasound images;

sum the sizes of the plurality of low echo regions to determine a size of the three dimensional region in a direction intersecting the two or more of the plurality of scanning surfaces; and cause the display to display a color image in a region of a B-mode image, wherein the B-mode image corresponds to one of the plurality of scanning surfaces, wherein the color image represents the three dimensional region within the one of the plurality of scanning surfaces, and wherein a color of the color image represents the size of the three dimensional region in a direction intersecting the two or more of the plurality of scanning surfaces.

15. The ultrasound diagnostic apparatus of claim 14, wherein the plurality of scanning surfaces are parallel to each other.

16. The ultrasound diagnostic apparatus of claim 15, wherein each of the plurality of scanning surfaces are in an XY-plane, and wherein the direction intersecting the two or more of the plurality of scanning surfaces is a Z direction, which is perpendicular to the XY-plane.

17. The ultrasound diagnostic apparatus of claim 15, wherein the processor is configured to determine the size of the three dimensional region in the direction intersecting the two or more plurality of scanning planes by summing a number of pixels corresponding to the three dimensional region in each of the two or more of the plurality of scanning surfaces.

\* \* \* \* \*